United States Patent [19]

Jadhav

[11] Patent Number: 5,352,811
[45] Date of Patent: Oct. 4, 1994

[54] METHOD OF PREPARING ALKANOYLOXYTETRODECANOIC ACID BY ASSYMMETRIC ALLYLBORATRON

[75] Inventor: Prabhakar K. Jadhav, Wilmington, Del.

[73] Assignee: E. I. Du Pont de Nemours and Company, Wilmington, Del.

[21] Appl. No.: 916,664

[22] Filed: Jul. 22, 1992

Related U.S. Application Data

[62] Division of Ser. No. 535,442, Jun. 8, 1990, Pat. No. 5,158,941.

[51] Int. Cl.$^5$ ............................................. C07C 51/00
[52] U.S. Cl. ..................................... 554/151; 554/150
[58] Field of Search ................ 554/150, 151; 514/558, 514/546, 547

[56] References Cited

U.S. PATENT DOCUMENTS 4,719,202  1/1988  van Boeckel et al. ............. 514/61

FOREIGN PATENT DOCUMENTS 172581  8/1985  European Pat. Off. .
04526  11/1984  PCT Int'l Appl. .

OTHER PUBLICATIONS

Jadhav Sep. 1993, Tetra hedron Letters, vol. 30, #36, pp. 4763–4766, 1989.
T. Shimizu et al., *Chem. Pharm. Bull.* 33(10):4621–4624 (1985).
M. Kiso et al., *Carbohydrate Research* 162:247–256 (1987).

*Primary Examiner*—Jose' G. Dees
*Assistant Examiner*—D. D. Carr

[57] ABSTRACT

Preparaing alkanoyloxytetradecanoic acids by asymmetric allylboration, acylation, and oxidation of homoallylic alcohols in the operational presence of a phase transfer catalyst.

4 Claims, No Drawings

METHOD OF PREPARING ALKANOYLOXYTETRODECANOIC ACID BY ASSYMMETRIC ALLYLBORATRON

This is a division of application Ser. No. 07/535,442, filed Jun. 8, 1990, now U.S. Pat. No. 5,158,941.

BACKGROUND OF THE INVENTION

1. Field of the Invention

This invention concerns the use of synthetic Lipid A analog P9132 to activate human monocytes. Activation of monocytes is useful in the stimulation of immune responses in the treatment of various diseases.

The Lipopolysaccharides (LPS) are a group of diverse lipid containing carbohydrates that exhibit a wide variety of biological activities. They occur naturally on the outer cell membranes of gram negative bacteria such as *Salmonella minnesota, Salmonella typhimurium* and *Escherichia coli*. Although the lipopolysaccharides are large molecules, most of their biological activities result from the activity of a small portion of the molecule known as Lipid A. The structure of Lipid A consists of two β(1,6)-linked D-glucosamine units with polar phosphate groups at 1 and 4' positions. The 2 and 2' amino positions and the 3 and 3' hydroxyl group are esterified with hydroxy fatty acids. It is known that natural Lipid A compounds are potent immunostimulants which cause various desirable effects but also some undesirable ones. Various synthetic analogues of Lipid A have been developed to avoid such undesirable effects as toxicity and pyrogenicity. The P9132 analog of Lipid A of the present invention has been found to stimulate the human monocyte to produce interleukin-1 (IL-1) and several other substances produced by activated monocytes and to inhibit the growth of tumor cells in mice. Because of its ability to activate monocytes and stimulate the production of IL-1 and TNF and because it is relatively non-toxic, P9132 may be useful in cancer therapy and to stimulate suppressed immune systems.

2. Background Art

Various Lipid A analogs have been synthesized.

Kiso et al., Carbohydrate Research, 162 (1987) 247–256, describe the synthesis of two types of optically active 4-O-phospho-D-glucosamine derivatives related to the non-reducing sugar subunit of bacterial Lipid A.

Tadayori Shimizu et al., Antitumor Activity and Biological Effects of Chemically Synthesized Monosaccharide Analogues of Lipid A in Mice, Chem. Pharm. Bull., 3, 10 (1985) 4621 et seq. synthesized five monosaccharide analogs of Lipid A and tested these against the ascites form of Ehrlich carcinoma and investigated their toxicity in mice.

International application PCT publication WO84/04526 teaches novel compounds which stimulate the immune cells in animals in a manner similar to Lipid A.

U.S. Pat. No. 4,719,202 discloses disaccharide and trisaccharide derivatives of Lipid A having immunomodulating properties. EP 172,581 describes the use of a Lipid A type disaccharide derivative for inducing mutagenic and tumor necrosis factor activities in a murine system. EP 143,840 describes the use of a monosaccharide Lipid A analog as an immunostimulant.

SUMMARY OF THE INVENTION

The present invention uses a synthetic Lipid A analog for the activation of human monocytes and for the inhibition of tumor cells in animals. The Lipid A analog (P9132) used is of the structure:

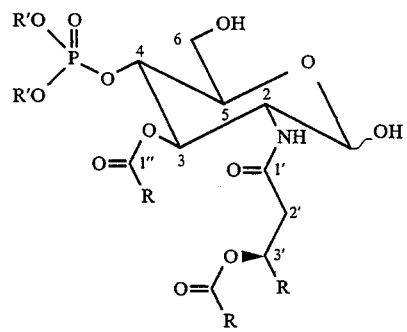

wherein:
Each R is a $C_6$–$C_{20}$ alkyl group;
R' is H, a trialkylammonium ion or an alkaline metal ion where stereoconfigurations at position 3' are (R) or (S) or combinations thereof or racemic.

It is an object of the present invention to describe a method for using Lipid A analog P9132, for the activation of human monocytes and for the inhibition of tumor cells.

DETAILED DESCRIPTION OF THE INVENTION

The present invention uses a synthetic analog of Lipid A, P9132, of the generalized structure described above for the activation of human monocytes and for the inhibition of tumor growth. Analog, P9132, can be synthesized by coupling a biantennary acid fragment of the structure (1) with glucosamine derivative (2):

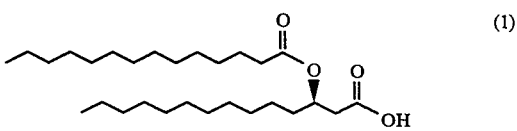

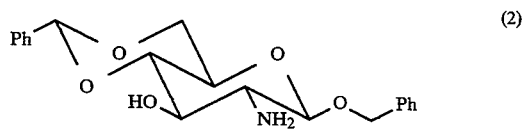

In the following discussion, the structures shown below are represented by the numbers indicated.

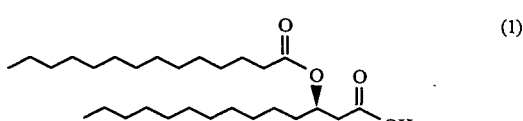

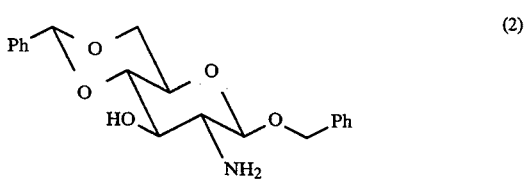

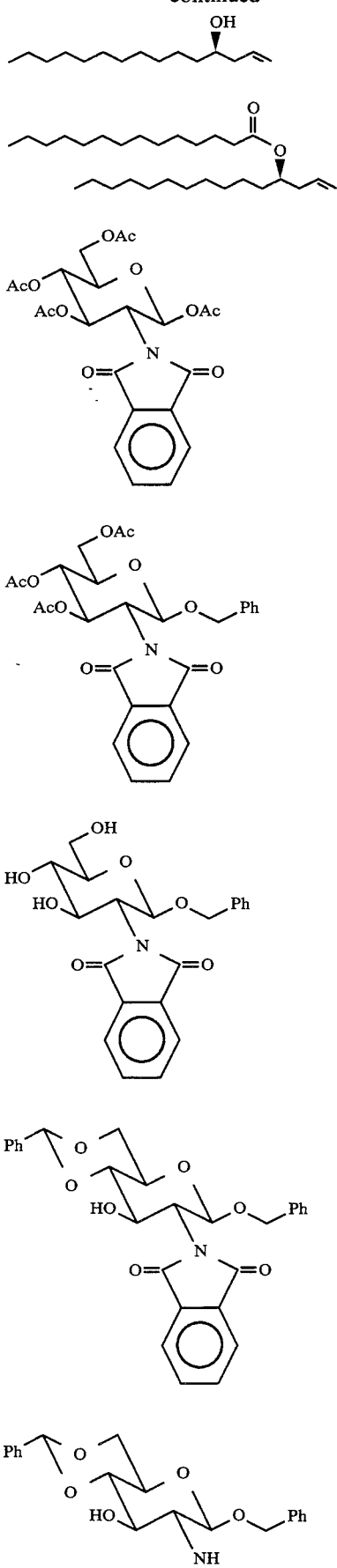

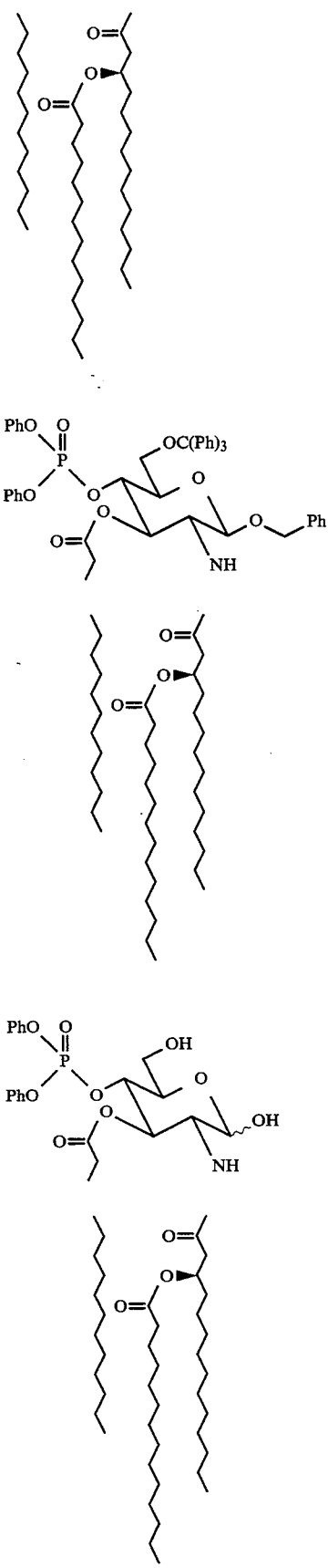
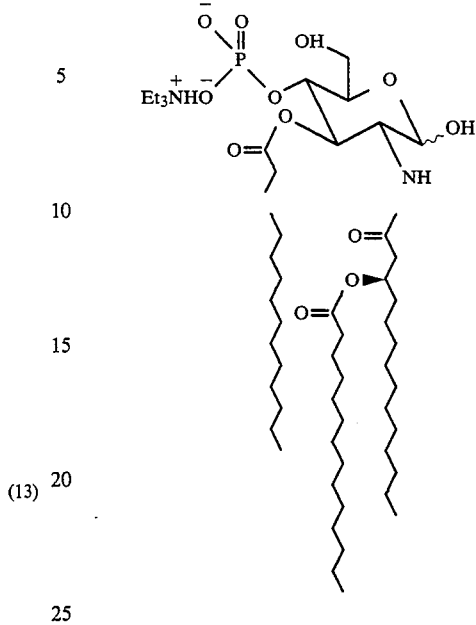

Biantennary acid fragment (1) can be synthesized from readily available dodecyl aldehyde.

There are various methods for enantioselective synthesis of 3-hydroxy acids. Most of these methods involve the synthesis of 3-keto esters followed by the reduction of the keto esters. A novel method of synthesizing the biantennary acid fragment involves the following steps:

(a) asymmetric allylboration of 1-dodecanal resulting in a homoallylic alcohol;

(b) acylation of the homoallylic alcohol; and (c) oxidation of the olefinic moiety to carboxylic acid in the optional presence of a phase transfer catalyst.

The oxidation of the olefinic moiety to carboxylic acid can be accomplished with permanganate. The acylation prior to permanganate oxidation not only protects the desired acyl group during oxidation but placement of the desired acyl group on 3-hydroxyl.

The asymmetric allylboration of 1-dodecanal with allyldiisopinocamphenylborane (derived from dextro-α-pinene), for example, provided, after oxidation of the intermediate borinate, a compound of structure (3) of greater than 99% enantiomeric purity. Compound (3) is acylated with tetradecanoyl chloride in the presence of pyridine to give a compound of structure (4). Compound 4 is then oxidized with potassium permanganate in the presence of a phase transfer catalyst to provide a desired biantennary acid of structure (1) in 66% overall yield from 1-dodecanal. The process described above for the synthesis of biantennary acid (1) is versatile and can be applied to the synthesis of the enantiomer (mirror image isomer) of (1) by selecting levo-α-pinene to prepare the allylboration reagent.

Glucosamine derivative (2) can be synthesized from readily available glucosamine hydrochloride as follows.

Glucosemine derivative (5) was synthesized from commercially available glucoamine hydrochloride using procedures reported by Lemieux et el., Advances in Chemistry, ACS Symposium Series 39:90 (1976).

Benzyl glycoside derivative (6) is prepared by contacting. (5) with benzyl alcohol in the presence of trimethylsilyl trifluoromethane sulfonate. Saponification of (6) furnished (7) which is converted to benzylidene derivative (8). This step is necessary because it allows the chemical differentiation of 3 different hydroxyl groups in (7). Finally, the phthalimido group in (8) is removed by treatment with hydrazine to provide desired (2).

The two fragments [(1) and (2)] prepared as described above were coupled in the presence of dicyclohexylcarbodiimide to provide compound of structure (9). This compound was then acylated with tetradecanoyl chloride to provide (10). Treatment of (10) with aqueous acetic acid resulted in the formation of (11). The two remaining hydroxyl groups in (11) were differentiated by treatment with trityl chloride in the presence of diisopropylethylamine. The resulting intermediate (12) is then phosphorylated with diphenyl phosphorochloridate to provide (13). Deprotection of the trityl and benzyl groups is achieved in one step by hydrogenolysis in the presence of palladium black and p-toluene sulfonic acid. Synthesis of (15) P9132 was completed by hydrogenolysis of phenyl groups in the presence of platinum oxide.

P9132 is prepared for testing in cell cultures and animals by dissolving it in a suitable solvent, preferably pyrogan-free dimethylsulfoxide (DMSO) then further diluting it with the medium of the cell culture to be treated or in a solution suitable for administration to animals. Where cell cultures are treated, the DMSO is further diluted so that its concentration in the mixture does not exceed about 1%. Diluted P9132, LPS, or Lipid A (the latter two compounds used as control stimulatory materials) are added to cell culture populations to be tested. Activation is determined by measuring the production of activation products. Inhibition of the growth of tumor cells in mice was determined by comparing tumor weight of treated and non-treated animals.

EXPERIMENTAL PREPARATIONS

Preparation of (R)-1-Pentadecen-4-ol (3)

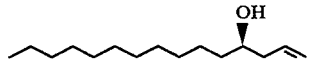

In a 250-ml round bottom flask equipped with septum inlet, bent tube adapter and magnetic stirring bar is placed (-)-B-chlorodiisopinocampheylborane (99% ee, 9.6 g, 30 mM derived from (+)-α-pinene). The reagent (purchased from Aldrich Chemical Co., 940 West Saint Paul Ave., Milwaukee, Wis. 53233), and 30 ml of anhydrous ether were placed under a nitrogen atmosphere. The mixture was cooled to −40° C. and then treated with allylmagnesium bromide (1.1M 22.7 ml, 25 mM). The reaction mixture was then allowed to warm to room temperature. Meanwhile, dodecanal (redistilled, 4.41 ml, 20 mM) was dissolved in 10 ml of anhydrous ethyl ether and cooled to ice-bath temperature (5° C.). The resulting allyldiisopinocampheylborane was cooled to −78° C. after stirring at room temperature for 30 minutes; dodecanal was then slowly added keeping the mixture at −78° C. The mixture was then allowed to warm to room temperature in the same bath overnight. The resulting mixture was cooled to 5° C. and then acetaldehyde (10 ml, 180 mM) was slowly added, with stirring. The mixture was further stirred at room temperature for 18 hours. The resulting organoborane was then oxidized at 5° C. with sodium acetate (20 ml, 60 mM), and hydrogen peroxide (30%, 10 ml). The addition of $H_2O_2$ generates an exothermic reaction. The mixture was extracted with diethylether ($Et_2O$) (3×20 ml), and the combined ether extracts were washed with water and a saturated solution of sodium chloride. The extract was dried over anhydrous magnesium sulfate, filtered and the solvent removed. The residue was chromatographed on silical gel (1:15 ethyl acetate/hexane). The pure fractions, as determined by thin layer chromatography (TLC) were pooled, made free of solvents and distilled to provide (R)-1-pentadecen-4-ol (3), a colorless oil with a bp 96° C., 0.5 mm of Hg, 3.39 g, 75% yield. Analysis of the prepared (R)-1-pentadecen-4-ol (3):

IR(neat) 3350, 2900, 2860, 1640, 910cm$^{-1}$. $^1$H NMR (CDCl$_3$) δ 0.89 (t, 3H, J=6.4Hz), 1.28 (bs, 16H), 1.47 (bs, 2H), 2.15 (m, 1H), 2.3 (bm, 1H), 3.65 (bq, 1H), 5.11 (s, 1H), 5.16 (d, 1H), 5.84 (m, 1H).

Preparation of (S)-1-Pentadecen-4-ol (+)-B-chlorodiisopinocampheylborane, as described by Brown et al., J. Amer. Chem. Soc. 105: 2092 (1983) and Jadhav et al., J. Org. Chem. 51: 432 (1986), was used to prepare the (S)-isomer. The experimental conditions for the preparation of (R)-1-pentadecen-4-ol were followed.

Preparation of (4R)-Tetradecanoyloxy-1-pentadecene (4)

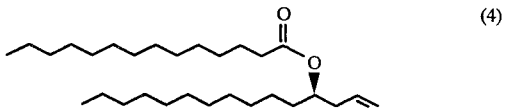

Under a nitrogen atmosphere, (4R)-1-pentadecen-4-ol (4.52 g, 20 mM) 50 ml of dichloromethane and 10 ml of pyridine was placed in a dry 250 ml round bottomed flask equipped with magnetic stirring bar, septum inlet, and bent tube adapter. With stirring, dodecanoyl chloride (Aldrich, 6.54 ml, 24 mM) was then added to the stirred mixture. The reaction mixture was stirred at room temperature for 18 hours (TLC, 1:4 ethylacetate/hexane). The reaction mixture was diluted with 50 ml of dichloromethane and washed with ice-cold 1M HCl followed by saturated sodium bicarbonate and brine. The residue after removal of solvent was chromatographed on silical gel (hexane) to provide 8.19 g, 94% yield of pure (R)-tetradecanoyloxy-1-pentadecene (J).

Analysis of the resulting (4R)-tetradecanoyloxy-1-pentadecene:

IR(neat): 2918, 1736, 1642, 1465, 1245, 1175, 915, 722cm$^{-1}$; $^1$H NMR (CDCl$_3$) δ 0.88 (t, 3H, J=6.4Hz), 1.25 (s, 42H), 1.58 (bm, 2H), 2.27 (t, 2H, J=7.5Hz), 4.92 (t, 2H, J=6.2Hz), 5.02 (s, 1H), 5.04 (d, 1H, J=7.5Hz), 5.74 (m, 1H).

Preparation of (3R)-tetradecanoyloxytetrsdecanoic acid (1)

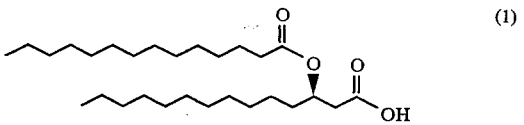

Potassium permanganate (8 g, 50 mmol) in 75 ml of water is placed in a 250 ml round bottomed flask with magnetic stirring bar and cooled to 5° C. Meanwhile, (4R)-tetradecanoyloxy-1-pentadecene (6.54 g, 15 mM) was dissolved in a solution of 75 ml of hexane and 15 ml of glacial acetic acid. Aliquat 36 (0.1 g) was added to the above solution and then the solution was added to the solution of potassium permanganate. The contents were stirred at 5° C. for 3 hours. Sodium sulfite (9 g) was added to the reaction mixture in order to decompose any excess permanganate. The resulting mixture was stirred for minutes and then acidified by adding 18 ml of (1:1 HCl/H$_2$O) hydrochloric acid. The aqueous layer was extracted with ethyl ether and the combined organic extract was washed with brine and dried. The residue after removal of solvent was chromatographed (5%; iPrOH in Hexane) to provide (3R)-tetradecanoyloxytetradecanoic acid (1), (6.39 g, 94%) as a colorless oil.

Analysis of (3R)-tetradecanoyloxytetradecanoic acid $^1$H NMR (CDCl$_3$) δ 0.88 (t, 3H J=6.5Hz), 1.25 (s, 42H), 1.65 (bm, 2H), 2.3 (bm, 2H), 2.65 (bm, 2H), 5.24 (bm, 1n).

Analysis of the Methyl Ester of (3R)-tetradecanoyloxtetradecanoic acid (prepared by diazomethane treatment)

IR(neat); 2922, 2858, 1745, 1468, 1170(cm$^{-1}$) $^1$H NMR (CDCl$_3$) δ 0.88 (t, 3H, J=6.4Hz), 1.25 (s, 42H), 1.58 (bs, 2H), 2.54 (d, H, J=3.7Hz), 2.65 (d, H, J=5.2Hz), 3.66 (s, 3H), 5.2 (m, 1H).

Preparation of 1,3,4,6-Tetra-O-acetyl-2-deoxy-2-phthalimido-β-D-glycopyranose (5)

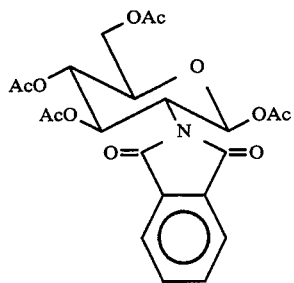

(5)

1,3,4,6-Tetra-O-acetyl-2-deoxy-2-phthalimido-β-D-glycopyranose (5) was prepared following the literature procedure of Lemieux, et al., Advances in Chemistry, ACS Symposium, Series 39:90 (1976).

Preparation of Benzyl 3,4,6-tri-O-acetyl-2-deoxy-2-phthalimido-β-D-glucopyranoside (6)

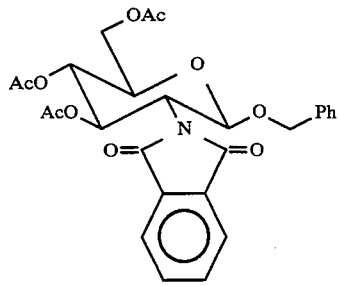

(6)

Under anhydrous conditions, 1,3,4,6-tetra-O-acetyl-2-deoxy-2-phthalimido-β-D-glucopyranose (5) (47.7 g, 100 mM), molecular sieves (4 Å) powder (20 g) and 250 ml of 1,2-dichloroethane and benzyl alcohol (12.5 ml, 120 mM) were placed in a dry 1 liter round bottom flask equipped with magnetic stirring bar, septum inlet and bent tube adapter. During a 5 minute period, trimethylsilyl trifluoromethane sulfonate (19.3 ml, 100 mM) was then added to the stirred mixture. The contents were stirred at room temperature for 16 hours. The reaction was found to be complete as evidenced by the products present on thin layer chromtography (TLC, 2:3 ethyl acetate:hexane). The reaction mixture was cooled in an ice-bath, quenched with saturated sodium bicarbonate and extracted with dichloromethane in the manner well known to those skilled in the art. The combined extract was washed with water, brine and dried over anhydrous magnesium sulfate. The residue after removal of solvent was purified by "flash chromatography" (silica gel, 500 g, solvent 1:3 ethyl acetate:hexane) to provide 40.6 g (85% yield) of benzyl 3,4,6-tri-O-acetyl-2-deoxy-2-phthalimido-β-D-glucopyranoside (6).

Analysis of benzyl 3,4,6-tri-O-acetyl-2-deoxy-2-phthalimido-β-D-glucopyranoside (6)

IR(KBr) 1750, 1715, 1385, 1230, 1040, 720 cm$^1$ $^1$H NMR (CDCl$_3$) δ 1.87 (s, 3H), 2.04 (s, 3H), 2.15 (s, 3H), 3.86 (m, 1H), 4.13 (m, 1H), 4.36 (m, 2H), 4.69 (AB, 2H, J=11Hz), 5.17 (dd, 1H, J=9.4Hz), 5.38 (d, 1H, J=8.5Hz), 5.78 (dd, 1H, J=9.4Hz), 7.06 (bs, 5H), 7.75 (bm, 4H).

Preparation of Benzyl 2-Deoxy-2-phthalimido-β-D-glucopyranoside (7)

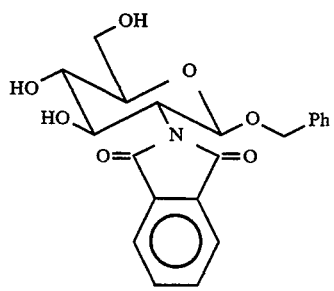

(7)

Benzyl 3,4,6-tri-O-acetyl-2-deoxy-2-phthalimido-β-D-glucopyranoside (3) (40.6 g, 84 mM) in 750 ml of dry methanol and 30 ml of 0.5M sodium methoxide was added to a 2 liter round bottomed flask equipped with magnetic stirring bar, saprum inlet and bent tube adapter and the contents stirred at room temperature for 18 hours. TLC indicated completion of the reaction. (The TLC solvent was 10:2:10 ethyl acetate: ethyl alcohol:hexane). To the mixture was added 15 g of Bio-Rad (Bio-Rad Laboratories, P.O. Box 708, 220Maple Ave., Rockville Center, N.Y. 11571) ion exchange resin AG-50W-X-8 (prewashed with H$_2$O, methanol, and dried) and stirred for 5 minutes (pH should be ≦7.0). The mixture, after filtration followed by the removal of solvent, furnished benzyl 2-deoxy-2-phthalimido-α-D-glucopyranoside (1), 30 g (89.4% yield).

Analysis of benzyl 2-deoxy-2-phthalimido-β-D-glucopyranoside (7)

IR(KBr) 3420, 1710, 1390, 1070, 1020, 720 cm$^{-1}$ $^1$H NMR (CDCl$_3$) δ 3.47 (m, 1H), 3.7 (m, 2H), 4.15 (m, 2H), 4.30 (dd, 1H), 4.65 (AB, 2H, J=11Hz), 5.23 (d, 1H, J=8.5Hz), 7.05 (bs, 5H), 7.72 (bm, 4H).

Preparation of Benzyl 4,6-O-Benzylidene-2-deoxy-2-phthalimido-β-D-glucopyranoside (8)

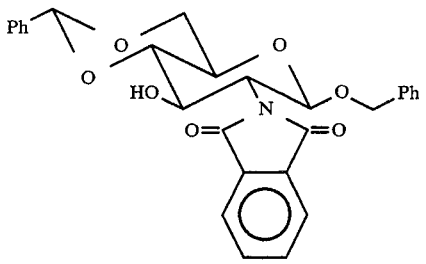

Benzyl 2-deoxy-2-phthalimido-β-D-glucopyranoside (7), (30 g, 75.12 mM) in 500 ml of dry acetonitrile was placed in a 1 liter round bottomed flask equipped with magnetic stirring bar, septum inlet and bent-tube-adapter. p-Toluene sulfonic acid (0.75 g) and dimethoxytoluene (34.95 ml, 225 mM) was then added to the solution. The reaction was complete after stirring the contents at room temperature for 1.5 hours. (TLC 10:1:10 ethyl acetate: ethyl alcohol:hexane). The reaction mixture was quenched with water and extracted with ethyl acetate. The combined organic extract was washed with saturated sodium bicarbonate, brine and dried over anhydrous magnesium sulfate. The mixture was crystallized from ethyl acetate:hexane 2:1 to provide 24.4 g of benzyl 4,6-O-benzylidene-2-deoxy-2-phthalimido-β-D-glucopyranoside (8). The mother liquor was chromatographed (1:1 ethyl acetate hexane) to furnish additional 7.34 g yield, 86.8%). of compound 8 (combined Analysis of benzyl 4,6-O-benzylidene-2-deoxy-2-phthalimido-β-D-glucopyranoside (8):

IR(KBr) 3440, 1715, 1390, 1100, 720 cm$^{-1}$: $^1$H NMR (CDCl$_3$) δ 3.60 (m, 2H), 3.83 (m, 1H), 4.27 (dd, 1H, J=9.4Hz), 4.40 (m, 1H), 4.66 (AB, 2H, J=11Hz), 4.60 (dd, 1H, J=9.4Hz), 5.26 (d, 1H, 8.5Hz), 7.05 (m, 5H), 7.36 (m, 3H), 7.50 (m, 2H), 7.72 (m, 4H).

Preparation of Benzyl 2-Amino-4,6-O-benzylidene-2-deoxy-β-D-glucopyranoside (2)

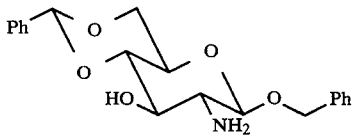

Benzyl 4,6-O-benzylidene-2-deoxy-2-phthalimido-β-D-glucopyranoside (8) (4.87 g, 10 mM) in 250 ml dry ethyl alcohol was placed in a 500 ml round bottomed flask equipped with saprum inlet, magnetic stirring bar and reflux condenser. The contents of the flask were degassed carefully to remove traces of oxygen and then filled with nitrogen. This operation was repeated three times. Hydrazine monohydrate (4.9 ml, 100 mM) was added to the mixture and the contents were then refluxed for three days. (Caution: Hydrazine is a cancer suspect agent!) The solvent and excess hydrazine were pumped off (under a vacuum of 1 mm of Hg) for 16 hours. The residue was washed with chloroform and filtered. The filtrate was dried and chromatographed (10:1:10) ethyl acetate:ethyl alcohol:hexane, to provide benzyl 2-amino-4,6-O-benzylidene-2-deoxy-β-D-glucopyranoside (Z) (3.155 g, 88.5% yield).

Analysis of benzyl 2-amino-4,6-O-benzylidene-2-deoxy-β-D-glucopyranoside (2):

IR(nujol mull) 3542, 3420, 2910, 2860, 1600, 1455, 1180, 1090, 1110, 995, 750$^{-cm}$ NMR (CDCl$_3$) 2.06 (bs, 2H, D$_2$O exchangable), 2.84 (t, 1H, J=11.2Hz), 3.43 (m, 1H), 3.54 (m, 2H), 3.78 (t, 1H, J=10Hz), 4.30 (dd, 1H, 5H2), 4.71 (AB, 2H, J=11Hz), 5.5 (s, 1H), 7.43 (m, 10H).

Preparation of ..Benzyl 4,6-O-Benzylidene-2-deoxy-2[[(3R)-tetradecanoyloxytetradecanamido ]-β-D-glucopyranoside (9)

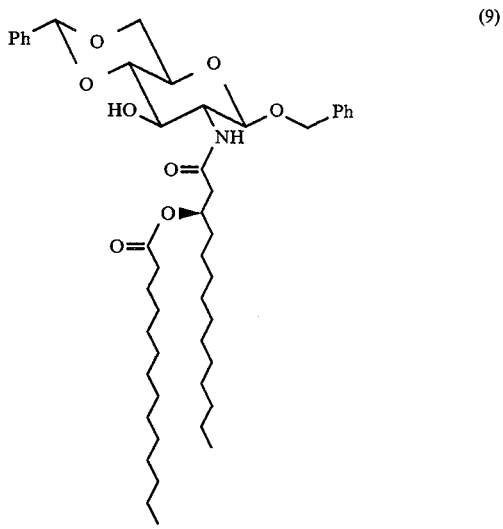

(3R)-Tetradecanoyloxytetradecanoic acid (1) (3.39 g, 7.48 mM) and benzyl 2-amino-4,6-O-benzylidene-2-deoxy-β-D-glucopyranoside (2) (2.664 g, 7.48 mM) in 75 ml of dry dichloromethane were placed in a 250 ml round bottomed flask. Dicyclohexylcarbodiimide (1.7 g, 8.23 mM) as a slurry in 25 ml of dichloromethane was added to the reaction mixture. The contents were stirred at room temperature for 2.5 hours (TLC 1: 1 ethyl acetate: hexane). The reaction mixture was diluted with dichloromethane and filtered. The solid was washed with 3 portions of dichloromethane (10 ml each). The combined filtrate was made free of solvents and the residue chromatographed (5% ethyl acetate in chloroform) to provide benzyl 4,6-O-benzylidene-2-deoxy-2-[(3R)-tetradecanoyloxytetradecanamido]-β-D-glucopyranoside (9) (4.369 g, 73.6% yield) as a white solid.

Analysis of benzyl 4,6-0-benzylidene-2-deoxy-2-[(3R)-tetradecanoyloxytetradecanamido]-β-D-glucopyranoside (9):

IR(KBr) 3440, 2920, 2860, 1730, 1653, 1100, 750, 700 cm$^{-1}$ $^1$H NMR (CDCl$_3$) δ 0.88 (t, 9H, J=6.5Hz), 1.26 (s, 42H), 1.58 (bs, 2H), 2.25 (t, 2H, J=7.2Hz), 2.41 (m, 2H), 3.56 (m, 2H), 3.83 (t, 1H, J=10Hz), 4.14 (m, H), 4.38 (dd, 1H, J=5Hz, J=9.4Hz), 4.76 (AB, 2H, J=11Hz), 4.80 (d, 1H, J=8.1Hz), 5.08 (m, 1H), 5.58 (s, 1H), 6.05 (d, 1H, J=7.1Hz), 7.5 (m, 10H).

Preparation of Benzyl 4,6-O-Benzylidene-2-deoxy-3-O-tetradecanoyl-2[(3R)-tetradecanoyloxy tetradecanamidol-β-D-glucopyranoside (10)

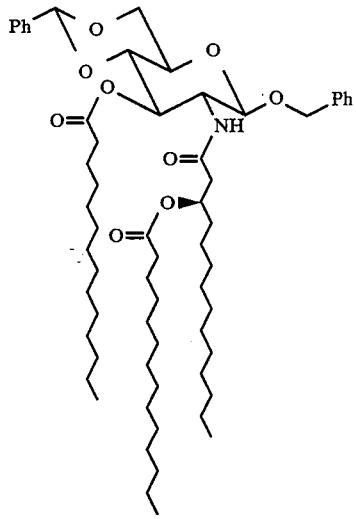

Benzyl 4,6-O-benzylidene-2-deoxy-2-[(3R)tetradecanoyloxytetradecanamido]-β-D-glucopyranoside (9) (2.28 g, 2.87 mM), 30 ml dry dichloromethane, 6 ml of pyridine and 60 mg of dimethylaminopyridine were placed in a 100 ml round bottomed flask. Tetradecanoyl chloride (0.96 ml, 3.6 mM) was then added to the stirred mixture and the contents stirred for 20 hours. The reaction was almost complete after 20 hours (TLC 2% ethyl acetate in dichloromethane). The reaction mixture was diluted with dichloromethane and the organic extract successively washed with ice-cold 1N HCl, water, saturated sodium bicarbonate and then with brine. The extract was dried over anhydrous magnesium sulfate, solvent was removed and the residue was chromatographed on silical gel (3% ethyl acetate in chloroform) to provide (2.101 g, 72.9% yield) of benzyl 4,6-O-benzylidene-2-deoxy-3-O-tetradecanoyl-2-[(3R)-tetradecanoyloxytetradecanamido]-β-D-glucopyranoside (10) as a waxy solid. Analysis of benzyl 4,6-O-benzylidene-2-deoxy-3-O-tetradecanoyl-2-[(3R)-tetradecanoyloxytetradecanamido]-β-D-glucopyranoside IR (KBr) 2920, 2850, 1740, 1660, 1100, 690, cm$^{-1}$ NMR (CDCl$_3$) δ 0.87 (t, 9H, 6.5Hz), 1.23 (s, 62H), 1.55 (bs, 2H), 2.34 (m, 6H), 3.52 (m, 1H), 3.71 (t, 1H), 3.82 (t, 1H), 4.14 (m, 1H), 4.37 (dd, 1H, J=6, 7Hz), 4.52 (d, 1H, J=9.7Hz), 4.70 (AB, 2H, J=10Hz), 5.04 (t, 1H, J-8Hz), 5.21 (dd, 1H, 9.8Hz), 5.5 (s, 1H), 5.87 (d, 1H, 9.8Hz), 7.36 (m, 1OH).

Preparation of Benzyl 2-Deoxy-3-tetradecanoyl-2-[(3R)-tetradecanoyloxytetradecanamido]-β-D-glucopyranoside (11)

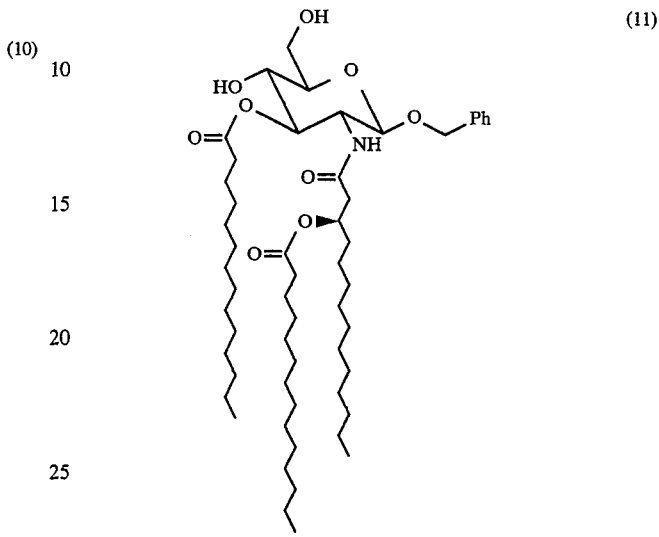

Benzyl 4,6-O-benzylidene-2-deoxy-3-O-tetradecanoyl-2-[(3R)-tetradecanoyloxytetradecanamido]-β-D-glucopyranoside (10) (1.913 g, 1.9 mM) in a mixture of glacial acetic acid (140 ml) and water (12 ml) were placed in a 250 ml round bottomed flask which was then placed in a bath heated to 100° C. for 0.5 hour. The reaction was complete as evidenced by TLC (solvent-20% ethyl acetate in chloroform). The mixture was cooled in an ice-bath and then diluted by adding water (750 ml). The mixture was extracted with dichloromethane (5×50 ml). The combined extract was carefully washed with saturated sodium bicarbonate, brine and then dried over magnesium sulfate. The residue, after all solvent had been removed, was chromatographed (30% ethyl acetate in chloroform) to provide benzyl 2-deoxy-3-tetradecanoyl-2-[(3R)-tetradecanoyloxytetradecanamido]-β-D-glucopyranoside (11) as a waxy solid (1.12 g, 64.2% yield).

Analysis of benzyl 2-deoxy-3-tetradecanoyl-2-[(3R)-tetradecanoyloxytetradecanamido]-β-D-glucopyranoside (11):

IR (KBr) 3300, 2920, 2855, 1735, 1655, 1555, 1465, 1070 cm$^{-1}$ $^1$H NMR (CDCl$_3$)δ 0.89 (t, H, J=6.4Hz), 1.30 (s, 62H), 1.55 (bs, 2H), 2.29 (m, 6H), 3.22 (m, 1H, H-5), 3.73 (t, 1H, J=9.56), 3.78 (dd, 1H, H-6), 3.93 (m, 2H, H-2, H-6), 4.65 (d, 1H, H-1, J=8Hz), 4.75 (AB, 2H, J=13Hz, OCH$_2$Ph), 5.01 (m, 2H, H-3, CHOCO), 5.87 (d, 1H, NH, J=10.6Hz), 7.31 (m, 5H).

Preparation of Benzyl 2-Deoxy-3-tetradecanoyl-2-[(3R)-tetradecanoyloxytetradecanamido]-6-O-trityl-β-D-glycopyranoside (12)

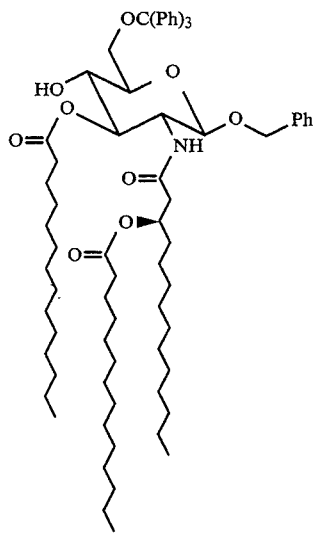

(12)

Preparation of Benzyl 2-Deoxy-4-O-(diphenylphosphono)-3-tetradecanoyl-2-[(3R)-tetradecanoyloxytetradecanamido]-6-O-trityl-β-D-glucopyranoside (13)

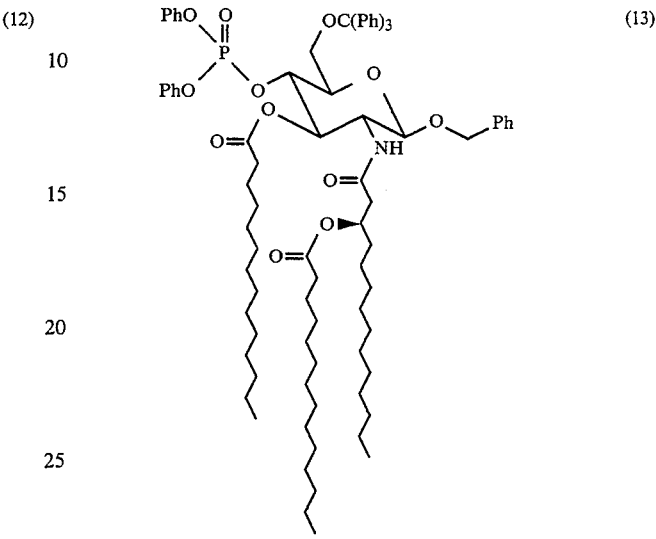

(13)

Benzyl 2-deoxy-3-tetradecanoyl-2-[(3R)-tetradecanoyloxytetradecanamido]-β-D-glucopyranoside (645 mg, 0.7 mmol) and trityl chloride (390 mg, 1.4 mmol) in 35 ml dry dichloromethane were placed in a 100 ml round bottomed flask equipped with a magnetic stirring bar, reflux condenser, and bent tube adapter. Diisopropylethylamine (0.49 ml, 2.8 mM) was then added to the mixture. The mixture was heated in an oil bath maintained at 65° C. for 1 hour (TLC 30% EtOAc/CHCl$_3$). The flask was cooled in an ice-bath then the mixture was diluted with dichloromethane. The organic layer was washed with water, brine and then dried. The residue, after the solvent was removed, was chromatographed on silica gel (1.5 EtOAc/hexane), to provide benzyl 2-deoxy-3-tetradecanoyl-2-[(3R)-tetradecanoyloxytetradecanamido]-6-O-trityl-β-D-glucopyranoside (12) as a waxy solid (700 mg, 86.3% yield).

IR (KBr) 3290, 2920, 2850, 1735, 1653, 1075, 700 cm$^{-1}$ $^1$H NMR (CDCl$_3$) δ 0.89 (t, 9H, J=6.5Hz), 1.26 (s, 62H), 1.58 (bs, 6H), 2.26 (t, 2H, J=6.5Hz), 2.31 (t, 2H, J=7Hz), 2.38 (m, 2H), 3.43 (m, 3H), 3.73 (t, 1H, J=10Hz, H-4), 4.05 (m, 1H), 4.49 (d, 1H, J=8.7Hz, H-1), 4.75 (AB, 2H, CH$_2$Ph, J=13Hz), 4.92 (dd, 1H, H-3, J=8.5Hz, J2=11Hz), 5.04 (m, 1H, —CHOCO), 5.74 (d, 1H NH, J=11Hz), 7.38 (m, 20H).

Benzyl 2-deoxy-3-tetradecanoyl-2-[(3R)-tetradecanoyloxytetradecanamido]-6-O-trityl-β-D-glucopyranoside (12) (115 mg, 0.1 mM) and dimethylaminopyridine (37 mg, 0.3 mM) in 2 ml of dry dichloromethane were put in a dry 10 ml round bottomed flask equipped with a magnetic stirring bar and a bent tube adapter. The mixture was placed under nitrogen, cooled in an ice-bath and stirred. Diphenyl phosphorochloridate (0.041 mL, 0.2 mM) was added to the stirred mixture at about 0° C. and the mixture was then allowed to warm to room temperature. After stirring the mixture at room temperature for 1 hour, (TLC 1:3 EtOAc: hexane) the excess diphenyl phosphorochloridate is quenched by adding methanol (8 μl, 0.2 mM) and then allowing it to stir at room temperature for 15 minutes. The solvents were removed end the residue was then chromatographed (50% ethyl acetate end hexane) to provide benzyl 2-deoxy-4-O-(diphenylphosphono)-3-tetradecanoyl-2-[(3R)-tetradecanoyloxytetradecanamido]-6-O-trityl-β-D-glucopyranoside (13) (107 mg, 76.9% yield). Analysis of benzyl 2-deoxy-4-O-(diphenylphosphono)-3-tetradecanoyl-2-[(3R)-tetradecanoyloxytetradecanamido]-6-O-trityl-B-D-glucopyranoside (13):

IR (KBr) 2900, 2850, 1750, 1730, 1648, 1490, 1295, 1190, 950 cm$^{-1}$ $^1$H NMR (CDCl$_3$) δ 0.89 (t, 9H, J=6.5Hz), 1.26 (s, 62H), 1.58 (bs, 6H), 2.25 (m, 6H), 3.41 (m, 1H), 3.61 (m, 2H), 4.6 (d, 1H, H-1), 4.72 (m, 1H), 4.87 (AB, 1H, J=11Hz), 5.04 (t, 1H), 5.12 (dd, 1H, J=9Hz ), 5.75 (d, J=8Hz, 1H), 6.82–700 (m, 30H); $^{31}$PNMR (CDCl$_3$): δ −11.92 (a, J=9Hz); FABMS 1391.23 (M$^+$+H) Calcd 1390.86.

Preparation of 2-Deoxy-4-O-(diphenylphosphono)-3-tetradecanoyl-2-[(3R)-tetradecanoyloxytetradecacanamidol-α,β-D-glycopyranose (14)

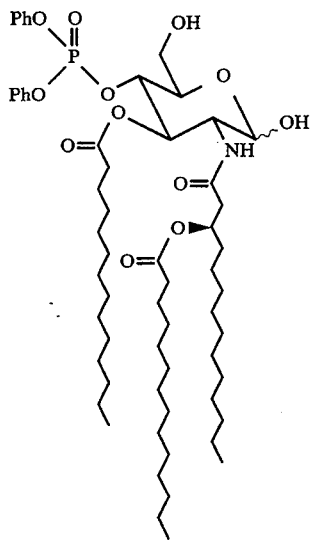

Benzyl 2-deoxy-4-O-(diphenylphosphono)-J-tetradecanoyl-2-[(3R)-tetradecanoyloxy tetradecanamidol-6-O-trityl-β-D-glucopyranoside (13) (836 mg, 0.601 mM), p-toluenesulfonic acid (5 mg), palladium black (200 mg) in 50 ml of absolute ethyl alcohol were put in a dry 100 ml round bottomed flask equipped with a magnetic stirring bar and bent tube adapter. The mixture was then exposed to hydrogen via a hydrogen balloon and stirred for 19 hours at room temperature. (TLC 1:2 ethyl acetate:hexane). The resulting mixture was filtered through a celite pad. The filtrate and washings were combined, taken to dryness and the resulting residue chromatographed (50% ethyl acetate in chloroform) to provide 2-deoxy-4-O-(diphenylphosphono)-3-tetradecanoyl-2-[(3R)-tetradecanoyloxytetradecacanamido]-α,β-D-glucopyranose (14) (391 mg, 61% yield). Analysis of 2-deoxy-4-O-(diphenylphosphono)-3-tetradecanoyl-2-[(3R)-tetradecanoyloxytetradecacanamido]-α,β-D-glucopyranose (14):

IR(KBr) 3340, 2920, 2855, 1733, 1650, 1490, 1200, 1045 cm$^{-1}$ $^1$H NMR (CDCl$_3$): δ 0.89 (t, 9H, J=6.5Hz), 1.26 (s, 62H), 1.58 (bs, 6H), 2.25 (m, 6H), 3.38 (m, 1H), 3.40 (m, 1H), 4.03 (m, 1H), 4.18 (t X d, 1H, J=4.2Hz, J=10Hz), 4.76 (9g, 1H, J=10.5Hz), 5.11 (t, 1H, J=6Hz), 5.27 (bs, 1H, H-1), 5.48 (dd, 1H, H-3, J=9Hz, J=10Hz), 6.09 (d, 1H, NM, J=9Hz), 7.29 (m, 10H); $^{31}$p NMR (CDCl$_3$): δ −11.01 (d, J=9.1Hz), −11.74 (d, J=10.01Hz); FABMS 1058.89 (M$^+$+H) Calcd 1058.70.

Preparation of 2-Deoxy-4-O-phosphono-3-tetradecanoyl-2-[(3R)-tetradecanoyloxytetradecanamidol-α,β-D-glucopyranose (P9132) (15)

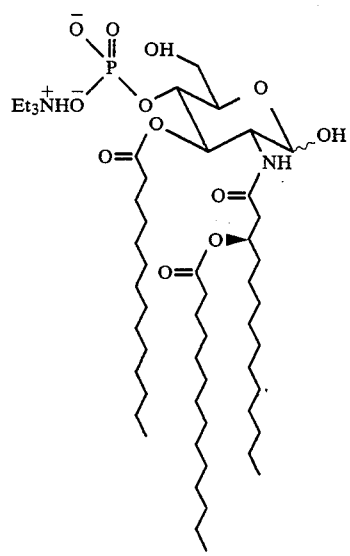

2-Deoxy-4-O-(diphenylphosphono)-3-tetradecanoyl-2-[(3R)-tetradecanoyloxytetradecanamido]-α,β-D-glucopyranose (14) (210 mg, 0.2 mM), platinum oxide (70 mg), 40 ml of 1:1 mixture of dry ethyl alcohol and methyl alcohol were put in a dry 100 ml round bottomed flask equipped with a magnetic stirring bar and a bent tube adapter. The mixture was then exposed to hydrogen by means of a hydrogen balloon and the mixture was stirred at 25° C. for 20 hours under the H$_2$ atmosphere. A white precipitate formed which was dissolved by adding triethylamine. The reaction was completed as evidenced by TLC (50% EtOAc in CHCl$_3$ and 50:25:4:2 CH$_2$Cl$_2$:MeOH:H$_2$O: NH$_4$OH). The mixture was filtered and the filtrate taken to dryness. The residue was suspended in pyrogen free water by sonication and the suspension was lyophilized to provide 250 mg of 2-deoxy-4-O-phosphono-3-tetradecanoyl-2-[(3R)-tetradecanoyloxytetradecanamido]-α,β-D-glucopyranose (P9132) (15). Analysis of 2-deoxy-O-phosphono-3-tetradecanoyl-2-[(3R)-tetradecanoyloxytetradecanamido]-α,β-D-glucopyranose (P9132) (15): $^{31}_p$ NMR (DMSO-D$_6$) 1.7965 (d, J=11 2Hz)

Preparation of LPS, Lipid A and P9132 for testing

The compound P9132 can he readily dissolved in dimethyl sulfoxide (DMSO). Preferably, the DMSO is pyrogen free. It can then be diluted in whatever medium the cell cultures to which it is to he added are in or a solution suitable for administration to animals. For addition to cell cultures, DMSO should be present at a concentration less than 1%. LPS may be obtained commercially. The preparations of lipopolysaccharide (LPS) used in the experiments of this invention were purchased from Calbiochem-Behring, (San Diego, Calif.), which had obtained them from *S. typhimurium.* Other sources of LPS are also acceptable. Synthetic lipid A molecules, mono- and bisphosphate form used in the experiments of the invention were purchased from ICN Biochemicals, Cleveland, Ohio. The purchased LPS and lipid A molecules are dissolved in pyrogen free water containing 0.1% triethylamine.

The LPS preparations serve as the control stimulatory material for monocyte activation and the stimulatory activity of P9132 is compared with that achieved by LPS and Lipid A.

Preparation of Human Monocytes

Peripheral human blood serves as the source of monocytes. The human monocytes for the experiments of this invention were obtained from leukopheresis units purchased from Biological Specialty Corp., Lansdale, Pa. Monocytes are selectively recovered by subjecting the cells in the units to a combination of Ficoll-Hypague density gradient centrifugation and centrifugal elutriation as described by Newton, J. Leukocyte Biol. 39:299–311 (1986). The resulting cell populations are 90–95% monocytes, lymphocytes and 4–5% neutrophils. Monocyte preparations are suspended in RPMI 1640 medium containing 5% fetal bovine serum (FBS) or other suitable media. Cultures for testing may be prepared by adding $1-2 \times 10^5$ monocytes contained in 100 μl to each well of a 96 well microtiter plate.

Testing of LPS, Lipid A and P9132 for Activation of Human Monocytes

LPS, Lipid A and P9132, to be tested for their ability to activate monocytes are added to the wells in 100 μl volumes. Activation of monocytes is determined by measuring increased production of the monocyte produced substances interleukin-1-β (IL-i-β), tumor necrosis factor-β(TNF-β), and prostaglandin E2 (PGE2). Medium (100 μl) is added to those wells not receiving any additional compounds. The cultures are then incubated overnight at 37° C. and the supernatant fluids collected and assayed.

The human IL-I-β and TNF-β produced are measured by means such as a capture Elisa assay protocol (Gaffnay et al., Biotechniques 5:652–657 (1987)). The PGE2 produced is measured by means such as a radioimmunoassay.

Preparation of Murine Peritoneal Macrophages

Murine macrophages can be obtained by washing the peritoneal cavities of normal BALB/c strain mice with 5 ml of Dulbecco's phosphate buffered saline (DPBS). Mice may be obtained from Charles River Laboratories, Wilmington, Mass. Cell populations obtained are typically about 70% macrophages. The cells are collected by gentle centrifugation, and resuspended in Dulbecco's minimal essential medium (DMEM) with 10% FBS and distributed into wells in a 96 well microtiter plate so that each well receives 100 μl of medium and $1.5 \times 10^5$ cells. After an hour, nonadherent cells can be removed by vigorously pipetting medium into the wells leaving adherent cells (macrophages).

To test LPS, Lipid A and P9132 for their ability to activate the murine macrophages, test substances are diluted in DMEM and 100 μl of each substance is added to appropriate wells. The cultures are incubated overnight at 37° C. at which time the supernatant fluids in the wells are individually collected and assayed for IL-1 biological activity using the thymocyte proliferation assay described by Krakauer et al., J. Immunol. 129:939–941 (1982).

EXAMPLE 1

Human Monocyte Stimulation

The compound P9132 was first tested for the ability to induce production of IL-1-β and PGE2 from human monocytes.

Human monocytes were obtained from leukopheresis units purchased from Biological Specialty Corp., Lansdale, Pa. Monocytes were selectively recovered by subjecting the cells in the units to a combination of Ficoll-Hypague density gradient centrifugation and centrifugal elutriation as described by Newton, J. Leukocyte Biol., 39:299–311 (1986). The resulting cell populations were 90–95% monocytes. The preparations were contaminated, by about 2–3% lymphocytes and 4–5% neutrophils. Monocyte preparations were suspended in RPMI 1640 medium containing 5% fetal bovine serum (FBS) and $1-2 \times 10^5$ cells were placed in each well of a 96 well microtiter plate in 100 μl of medium.

Compounds to be tested for their ability to activate human monocytes were diluted in RPMI 1640 medium with 5% fetal bovine serum then added to the wells of the monocyte-containing microtiter plates in 100 μl volumes. Medium (RPMI 1640 containing 5% FBS) (100 μl) was added to those wells not receiving any additional compounds. The cultures were then incubated overnight at 37° C. at which time the supernatant fluids were collected and assayed. Human IL-1-β production was measured using a capture Elisa assay protocol as described by Gaffnay et al., Biotechniques 5:652–657 (1987). PGE2 production was measured by radioimmunoassay.

The results from the above described experiments are shown in Table 1.

TABLE 1

| Concentration | IL-1-β (ng/ml) produced | |
|---|---|---|
| | P9132 | LPS |
| 1 μg/ml | 7.73 (±2.30)* | 2.48 (±0.29) |
| 100 ng/ml | 5.30 (±0.50) | 3.43 (±0.57) |
| 1 ng/m; | 0.00 | 1.93 (±0.23) |
| 100 pg/ml | 0.00 | 0.45 (±0.11) |

*Numbers in parentheses are standard deviations

From this experiment, it can be seen that, in contrast to the broad dose response seen with LPS, P9132 demonstrates a sharp and defined dose response curve. P9132 induced between 1.3 and 3.1 fold greater amounts of IL-1-β production by monocytes than a comparative amount of LPS.

A dose response curve over a narrower range of concentration is shown in Table 2.

TABLE 2

| Concentration of P9132 or LPS (ng/ml) | IL-1-β (ng/ml) produced | |
|---|---|---|
| | P9132* | LPS* |
| 1000 | 16.8 (±1.26) | 2.57 (±0.25) |
| 500 | 18.0 (±4.77) | NT |
| 250 | 5.75 (±0.49) | NT |
| 100 | 0.12 (±0.02) | 1.53 (±0.23) |
| 50 | 0 | NT |
| 25 | 0 | NT |
| 10 | NT | 1.04 (±0.06) |
| 1 | NT | 0.63 (±0.03) |

NT = not tested
*numbers in parentheses are standard deviations

The EC$_{50}$ value obtained for P9132 relative to LPS from such experiments is approximately 200 ng/ml.

EXAMPLE 2

The compounds of this Example are salts of P9132, two preparations of Lipid A and two preparations of LPS, one from *E. coli* and the other from *S. typhi*. The compounds were tested for their ability to activate human monocytes as described in Example 1. The results are the values of the optical density (405 nm) readings resulting from the capture Elisa assay of Example 1.

| Conc. (μg/ml) | Free Acid | Triethyl-amine | Ammon Salt | Diiso-propyl | Triiso-propyl |
|---|---|---|---|---|---|
| 10    | 2.074 | 2.004 | 2.191 | 2.244 | 2.235 |
| 5     | 1.775 | 1.802 | 1.906 | 2.049 | 2.219 |
| 2.5   | 1.068 | 1.089 | 1.306 | 1.302 | 1.375 |
| 1.0   | 0.678 | 0.363 | 0.669 | 0.544 | 0.481 |
| 0.5   | 0.226 | 0.209 | 0.496 | 0.319 | 0.111 |
| 0.25  | 0.139 | 0.084 | —     | 0.330 | 0.192 |
| 0.1   | 0.104 | 0.106 | 0.225 | 0.113 | 0.156 |
| 0.05  | 0.109 | 0.107 | 0.190 | 0.112 | 0.167 |

| Conc. (μg/ml) | Lipid A #25972 | Lipid A #25973 |
|---|---|---|
| 10   | 0.223 | 0.275 |
| 5    | 0.162 | 0.194 |
| 2.5  | 0.145 | 0.191 |
| 1.0  | 0.135 | 0.179 |
| 0.5  | 0.123 | 0.173 |
| 0.25 | 0.116 | 0.172 |
| 0.1  | 0.113 | 0.155 |

| Conc. (ng/ml) | LPS *E. coli* | LPS *S. typhi* |
|---|---|---|
| 1000 | 1.571 | 2.749 |
| 100  | 0.837 | 2.134 |
| 10   | 0.844 | 1.641 |
| 1    | 0.183 | 0.911 |
| 0.1  | 0.118 | 0.144 |
| 0.01 | 0.138 | 0.141 |

The results show that all the salts of P9132 stimulate IL-1-$\beta$ production by monocytes better than does Lipid A at all concentrations. P9132, however, was not more potent a stimulator than either preparation of LPS.

EXAMPLE 3

Stimulation of human TNF-$\beta$

P9132 and LPS were compared for their ability to stimulate the production of human TNF-$\beta$ by human monocytes using the procedures described in Example 1. The results are shown in Table 3.

TABLE 3

| Material Added to Monocytes | TNF-$\beta$ (O.D.)* |
|---|---|
| none | .02 (±.007) |
| 10 ng/ml LPS | .229 (±.023) |
| 10 ng/ml of P9132 | .006 (±.006) |
| 30 ng/ml of P9132 | .012 (±.009) |
| 100 ng/ml of P9132 | .031 (±.009) |
| 300 ng/ml of P9132 | .122 (±.135) |
| 1 μg/ml of P9132 | .104 (±.027) |
| 3 μg/ml of P9132 | .167 (±.025) |
| 10 μg/ml of P9132 | .162 (±.011) |

O.D. = optical density at 405 nm
*numbers in parentheses are standard deviations P9132 stimulated the production of TNF-$\beta$ by human monocytes, but was less effective than LPS at equivalent concentrations.

EXAMPLE 4

Stimulation of PGE2

Human monocytes also produce PGE2 when they are stimulated with LPS. To see how effectively P9132, relative to LPS, stimulates PGE2 production, human monocytes were stimulated with P9132 and LPS as described in Example 1. The results are shown in Table 4.

TABLE 4

| Concentration of P9132 or LPS (ng/ml) | PGE2 (pg/ml) produced | |
|---|---|---|
| | P9132* | LPS* |
| 1000 | 1933 (±348) | 2566 (±176) |
| 500  | 1661 (±368) | NT |
| 250  | 221 (±66)   | NT |
| 100  | 97 (±56)    | 1824 (±237) |
| 50   | 0           | NT |
| 25   | 0           | NT |
| 10   | NT          | 1491 (±108) |
| 1    | NT          | 982 (±89) |

NT = not tested
*numbers in parentheses are standard deviations

A dose response similar to that seen for IL-1-$\beta$ induction was obtained for both compounds. However, in contrast to its stimulation of the production of IL-1-$\beta$, P9132 did not stimulate production of greater amounts of PGE2 compared to the amounts stimulated by equivalent concentrations of LPS.

EXAMPLE 5

Stimulation of Murine Macrophages

P9132 was compared with LPS in its ability to stimulate murine macrophages to produce murine interleukin-1 (IL-1).

Murine macrophages were obtained by washing the peritoneal cavities of normal BALB/c strain mice with 5 ml of Dulbecco's phosphate buffered saline (DPBS). The cell population obtained was about 70% macrophages. The cells were collected by gentle centrifugation, and resuspended in Dulbecco's minimal essential medium (DMEM) with 10% FBS and distributed into wells in a 96 well microtiter plate so that each well received 100 μl of medium and 1.5×10$^5$ cells. After an hour, nonadherent cells were removed by vigorously pipetting medium into the wells which left adherent cells (macrophages) remaining. LPS and P9132 were diluted in medium and 100 μl of each dilution of each substance were added to appropriate wells. The cultures were incubated overnight at 37° C. and the supernatent fluids were collected and assayed for IL-1 biological activity using the thymocyte proliferation assay described by Krakauer et al., J. Immunol. 129:939–941 (1982).

The results shown Table 5 were obtained.

TABLE 5

| Concentration of P9132 or LPS (ng/ml) | IL-1 (units/ml) produced | |
|---|---|---|
| | P9132* | LPS* |
| 10000 | NT          | 18.2 (±2.3) |
| 1000  | 1.5 (±0.3)  | 13.4 (±0.7) |
| 500   | 1.5 (±1.6)  | NT |
| 250   | 2.6 (±0.9)  | NT |
| 100   | 0.7 (±0.2)  | NT |
| 50    | 0.5 (±0.2)  | NT |
| 25    | <0.1        | NT |

NT = not tested
*numbers in parentheses are average ± standard deviations

While doses of 50–1000 ng/ml induced detectable levels of In-1 activity from these cells, the levels obtained were 5–10 fold lower than those obtained with LPS at equivalent concentrations. When both LPS and P9132 were added at concentrations of 1.0 µg/ml (1000 ng/ml) to cultures of murine macrophages, the LPS stimulated the production of about 6 times more murine In-1 than P9132 did.

It should be noted that murine macrophages are at least 1000 fold less sensitive than human monocytes to the effects of LPS.

EXAMPLE 6

Comparison of P9132 with other Synthetic Lipid A Molecules

The P9132 molecule is a synthesized molecule modeled on the structure of the lipid A core of *S. minnesota* LPS. It has been reported that the activity of the LPS molecule from this species is attributable to the lipid A component (Luderitz et al., Rev. Infect. Dis. 6:428–431 (1984)). Synthetic lipid A preparations based on the *S. minnesota* LPS structure (obtained commercially) were compared with P9132 for their ability to stimulate IL-i-$\beta$, TNF-$\beta$, and PGE2 in human monocytes. Human monocytes were obtained and incubated with these compounds as described in Example 1. The results are shown in Table 6.

TABLE 6

| Material Added to Monocytes | | Substance Produced by Monocytes | | |
|---|---|---|---|---|
| (µg/ml) | Substance | IL-1-$\beta$ (O.D.) | TNF-$\beta$ (O.D.) | PGE2 (pg/ml) |
| none | none | 0.001 ($\pm$0.006) | 0.020 ($\pm$0.007) | 78 ($\pm$78.0) |
| 1 | Lipid A monophosphate | 0 ($\pm$0.004) | 0.007 ($\pm$0.001) | 66 ($\pm$40.0) |
| 10 | Lipid A monophosphate | 0.046 ($\pm$0.009) | 0.044 ($\pm$0.017) | 100 ($\pm$8.0) |
| 1 | Lipid A biphosphate | 0.209 ($\pm$0.027) | 0.061 ($\pm$0.006) | 267 ($\pm$22.0) |
| 10 | Lipid A biphosphate | 0.212 ($\pm$0.020) | 0.068 ($\pm$0.017) | 311 ($\pm$54.0) |
| 1 | P9132 | 0.322 ($\pm$0.035) | 0.104 ($\pm$0.027) | 487 ($\pm$17.0) |
| 10 | P9132 | 0.457 ($\pm$0.023) | 0.162 ($\pm$0.162) | 1184 ($\pm$116.0) |
| 0.01 | LPS | 0.766 ($\pm$0.066) | 0.229 ($\pm$0.023) | 2015 ($\pm$138.0) | numbers in parentheses are average $\pm$ standard deviations

It is apparent that the P9132 molecule more efficaciously stimulated the production of IL-1-$\beta$, TNF-$\beta$ and PGE2 than the mono- or bisphosphate forms of synthetic Lipid A did.

EXAMPLE 7

This example is to show that P9132 is relatively nontoxic in comparison to LPS when administered to mice.

We first established that adrenalectomized mice die when they are injected with only very small amounts of LPS (i.e., 3.6 µg per Kg) while sham operated mice show no effect to LPS injections of up to 10 mg per Kg.

Male CD1 mice, some adrenalectomized and some sham operated, weighing between 20 and 22 grams were purchased from Charles River Italia, 22050 Calco (CO), Italy, and used in the tests below when at least two weeks had transpired since the surgery had been done and when they weighed between 28 and 32 grams.

The chemicals to be tested were prepared at concentrations so that each mouse could be injected intravenously with 10 µL per g of mouse weight. Compound P9132 (10 mg per mL) was dissolved in pyrogan free dimethylsulfoxide and dilutions were made in sterile physiological saline. Adrenalectomized and sham operated mice were injected intravenously with dimethylsulfoxide, 10 µg/kg of LPS and between 10 and 10,000 µg/kg of P9132 and the number of dead animals was recorded 24 h later and for an additional week. The LPS used was *E. coli* serotype 055:B5 and it was purchased from Difco (Difco Laboratories, Detroit, Mich.).

| | Results: | | |
|---|---|---|---|
| | Amount | Number of Mice Dead at 24 h | |
| Compound | injected[1] | ADX[2] | SO[3] |
| DMSO[4] | | 0/5[5] | 0/5[5] |
| LPS | 10 | 9/11 | 0/5 |
| P9132 | 10 | 0/5 | 0/5 |
| | 100 | 0/5 | 0/5 |
| | 500 | 0/5 | 0/5 |
| | 1000 | 0/5 | 0/5 |
| | 10000 | 1/10 | 0/5 |

[1]µg per kg injected intravenously into each mouse
[2]ADX = adrenalectomized mice
[3]SO = sham operated mice
[4]DMSO = dimethylsulfoxide
[5]number of mice dead/number of mice injected
Conclusion: P9132 is at least 1000 fold less toxic in adrenalectomized mice than is LPS.

EXAMPLE 8

This example shows that P9132 inhibited the growth of tumor cells in mice.

For these experiments, female C57BL/6 mice from Charles River Laboratories, Wilmington, Mass., and B16 melanoma cells obtained from the NCI Tumor Repository (Frederick, Md) were used. The B16 melanoma cells were negative for viruses (ascertained by MAP tests) and were mycoplasma free. They were grown in RPMI 1640 medium (Gibco, Grand Island, N.Y.) supplemented with 10% fetal calf serum (Hyclone, Logan, Utah).

B16 tumor cells were suspended in phosphate buffered saline at a concentration of $1 \times 10^6$ cells/mL. Mice were injected intradermally on their ventral surfaces with 0.1 mL of the cell suspension. Tumors grew in 100% of the mice. Groups of 8 mice, randomly selected, all with tumors weighing more than 200 mg were selected for treatment. P9132, (100 µL, 100 µg in DMSO, then further diluted in physiologic saline) was administered directly into the tumor mass (intratumorally). Mice received similar injections of P9132 each day for 5 days on days 13 to 17 after they were inoculated with the tumor cells. Also, groups of 8 mice, randomly selected, with tumors weighing more than 200 mg to serve as controls were injected with just the solvent and diluent (dimethylsulfoxide and physiologic saline) used to prepare the P9132 for injection. Tumor weights (in mg) were calculated daily by the formula: $0.5 \times (w2 \times 2)$, where W and L represent the width and length (in mm) of the tumor. Tumor weights were determined by weighing on the 18th day when the experiment was terminated and the mice were sacrificed. Inhibition (in %) of tumor growth equals $(1-(T-S/C-S)) \times 100$, where T and C represent the mean tumor weight of the treated and control groups and S represents the mean starting weight. The Student's t-test was used for statistical analysis using the Balance software program (Elsevier Scientific Software, Amsterdam, Netherlands).

Results

The increase in average tumor weight which occurred in the control mice (from about 250 mg to about 1350 mg) was inhibited by 50–66 percent in the group of mice which received P9132 injected directly into the tumor masses.

EXAMPLE 9

This example was performed just as the preceding example except that P9132 was injected not only directly into the tumor but in one group of tumor bearing mice, also intradermally on the right ventral side.

Results

The increase in average tumor weight which occurred in the control mice (from about 200 mg to about 1300 mg) was inhibited by 47–60 percent in the group of mice which received P9132 injected directly into the tumor masses.

However, the increase in tumor weight in the mice which received P9132 intradermally was not significantly inhibited (i.e., from about 200 mg to about 1200 mg). While it is not known why P9132 was not effective when injected intradermally, it may be (1) due to dilution in the body, (2) due to inactivation by inhibitors in body fluids, or failure to recruit and/or activate macrophages or other cells to the site of the tumor.

The foregoing Examples are intended to exemplify but not to limit the invention. It is understood that this invention is not limited to the specific embodiments shown but is only limited as described by the claims appended hereto.

What is claimed is:

1. A process for synthesizing a compound of structure:

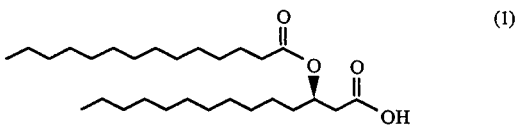

comprising the following steps:
 (a) asymmetric allylboration of 1-dodecanal resulting in a homoallylic alcohol;
 (b) acylation of the homoallylic alcohol; and
 (c) oxidation of the olefinic moiety to carboxylic acid in the optional presence of a phase transfer catalyst.

2. The process of claim 1 wherein the oxidation of the olefinic moiety to carboxylic acid is done with permanganate.

3. The process of claim 1 wherein the allylboration of 1-dodecanal is done with allyldiisopinocamphelborane derived from dextro-α-pinene.

4. The process of claim 1 wherein the allylboration of 1-dodecanal is done with an allylboration reagent synthesized from levo-α-pinene.

* * * * *